United States Patent [19]

Cooper et al.

[11] Patent Number: 5,055,478

[45] Date of Patent: Oct. 8, 1991

[54] METHOD FOR STOPPING SMOKING

[76] Inventors: Thomas M. Cooper, 826 Glendover Cir.; Richard R. Clayton, 3414 Coldstream Ct., both of Lexington, Ky. 40502

[21] Appl. No.: 146,397

[22] Filed: Jan. 21, 1988

Related U.S. Application Data

[63] Continuation-in-part of Ser. No. 876,240, Jun. 19, 1986.

[51] Int. Cl.$^5$ ................. A61K 9/68; A61K 31/465
[52] U.S. Cl. ..................... 514/343; 424/48; 424/440; 426/3; 131/270; 514/813
[58] Field of Search ............... 514/343, 813; 424/48, 424/440; 131/270

[56] References Cited

U.S. PATENT DOCUMENTS

| | | | |
|---|---|---|---|
| 3,862,317 | 1/1975 | Lal Anans | 514/813 |
| 3,870,794 | 3/1975 | Hutchinson et al. | 514/343 |
| 4,579,858 | 4/1986 | Ferno et al. | 514/343 |
| 4,597,961 | 7/1986 | Etscorn | 514/813 |

OTHER PUBLICATIONS

Malcolm Psychopharmacology 70(3):295-296 (1980).
Hughes Psychopharmacology 83(1):82-87 (1984).
McNabb Can. Med. Assoc. J. 131(6): 589-592 (1984).
Jarvis Brit. Med. J. 285(6431):537-540 (1982).
Crofton Brit Med. J. 268(6365):59597(1983).
Jambrozik Brit. Med. J. 289(6448):794-797 (1984).
Clavel Brit. Med. J. 291(6508) 1532-1539 (1985).
Hughes J. A. M. A. 252 (20) 2855-2858(1984).
Brantmark et al. Psychopharmacologia 31: 191-200 (1973).
Russell et al., Brit. Med. J. (2)14 Aug. 1976: 391-393.
Turner Postgrad. Med. J. 53: 683-685 (1977).

*Primary Examiner*—Shep K. Rose
*Attorney, Agent, or Firm*—King & Schickli

[57] ABSTRACT

A method for eliminating an individual's tobacco smoking habit and associated nicotine dependence includes the step of gradually decreasing tobacco consumption over a first period of time until no further tobacco is consumed. This is done by first recording the individual's daily tobacco consumption. The day is broken down into consumption periods of one hour each. An alternative oral nicotine source is then progressively administered as a substitute for tobacco consumed during sequential consumption periods over each succeeding day for approximately two weeks until no further tobacco is consumed. Following a period during which the administration of the alternative nicotine source is maintained, it, too, is progressively eliminated over a period of approximately sixteen weeks.

12 Claims, 2 Drawing Sheets

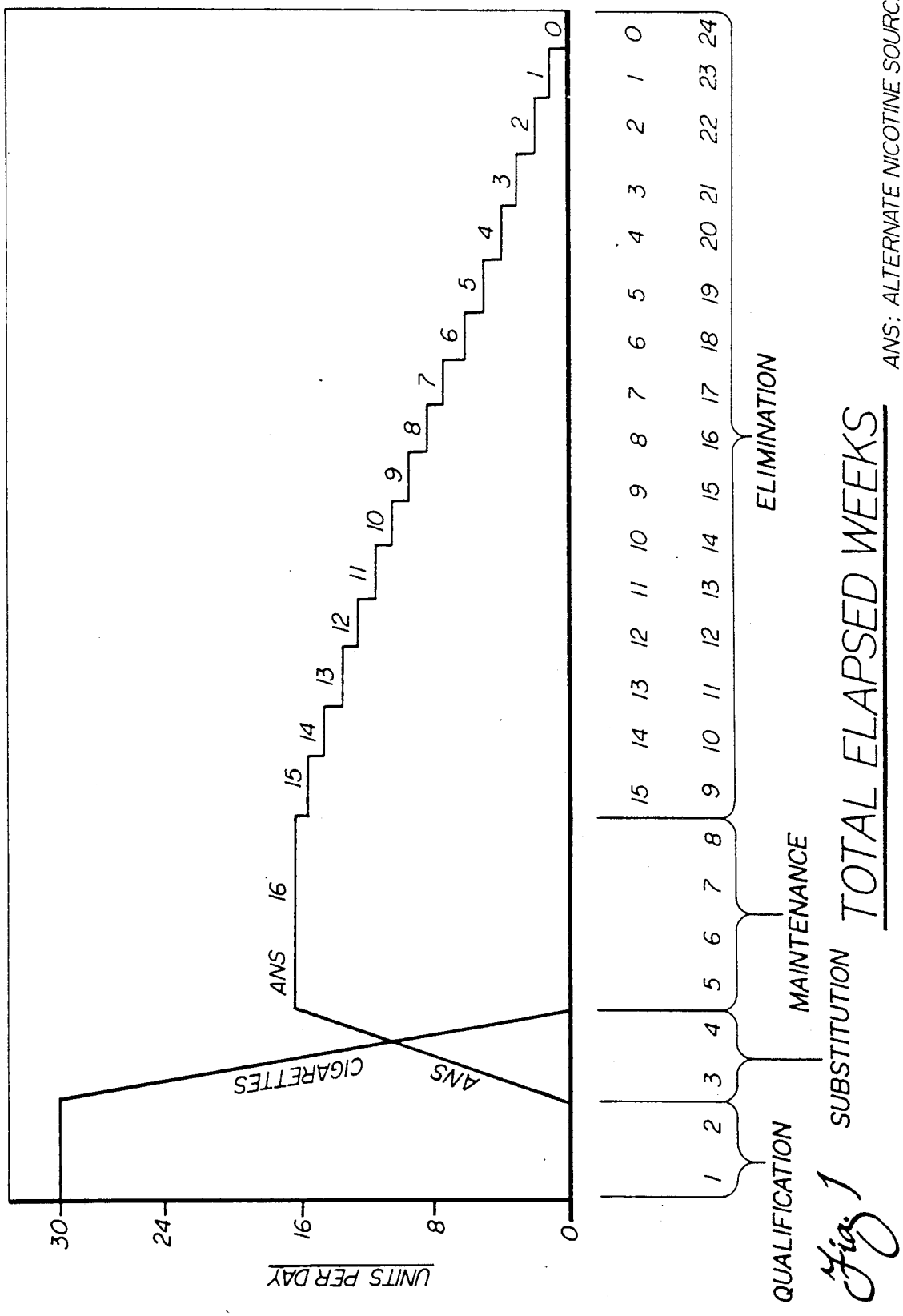

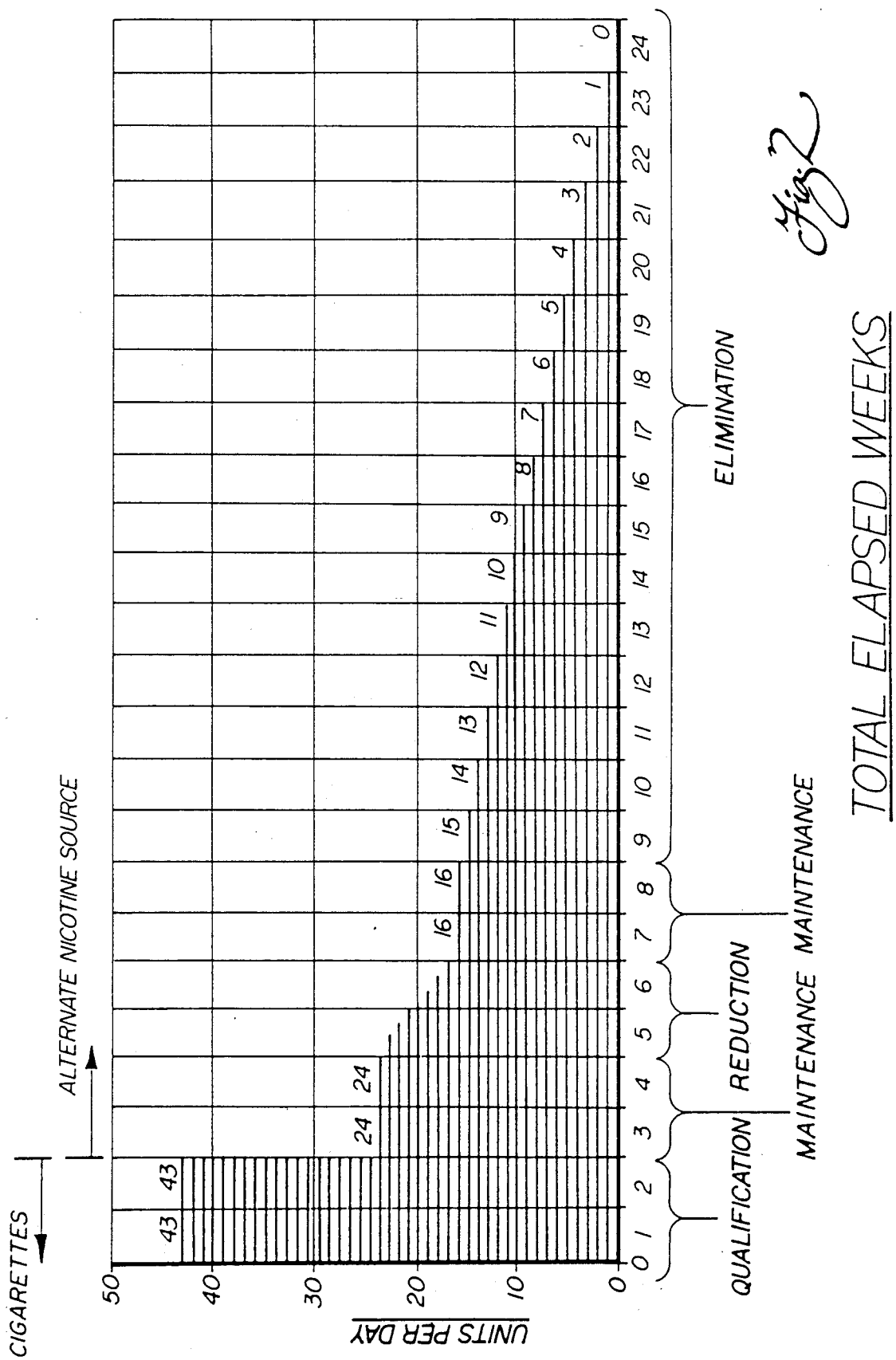

METHOD FOR STOPPING SMOKING

This is a continuation-in-part of application Ser. No. 876,240, filed on June 19, 1986.

BACKGROUND OF THE INVENTION

The present invention relates to an improved method of eliminating an individual's tobacco smoking habit as well as the associated nicotine dependence created by smoking.

The use of tobacco and, more particularly, the smoking of cigarettes is well recognized as a major public health problem. Tobacco use has been irrefutably tied to such ailments as cardiovascular disease, emphysema and various forms of cancer. Yet, despite the ever growing evidence linking tobacco use to very serious diseases and the warnings of the U.S. Surgeon General on cigarette packaging, tobacco use persists. This is true even though there is a high public awareness of the problem.

Many present day tobacco smokers recognize the danger and appreciate the need to overcome their tobacco dependence. There, however, is a large difference between recognizing the need to overcome tobacco dependence and actually overcoming the dependence. The difficulty in overcoming the tobacco dependence is best illustrated by the number of different methods that have been designed to aid people in reaching this goal.

One of the methods utilized is psychotherapeutic in nature and includes the utilization of hypnosis. Another known method is negative conditioning. For example, an apparatus is rigged on the individual so that whenever reaching for a cigarette, the individual is subjected to a painful stimuli, such as an electrical shock. An additional alternative is a pharmacological approach. This involves the administration of a therapeutic compound, such as Lobeline or other sedatives or anti-convulsant drugs. Whether used separately or in various combinations, these prior art methods have only met with limited success.

More recent study of the smoking problem has led to the development of nicotine substitutes as anti-smoking aids. Such a substitute is marketed as a chewing gum under the trademark Nicorette by Merrell-Dow of Cincinnati, Ohio. As a general practice, the prior art teaches that alternative nicotine sources are only effective as an anti-smoking aid when an individual immediately stops smoking and substitutes the nicotine source for the cigarettes. In fact, up until the development of the method of the present invention, insofar as I am aware there has been no suggestion that a gradual cutting of tobacco consumption with the substitution of an alternative nicotine source might be an effective approach to overcoming tobacco dependency.

While this approach to immediately stop smoking by taking a substitute nicotine source and going cold turkey on smoking is successful for certain individuals, the results are not satisfactory for the large majority of addicted smokers. One theory is that suddenly giving up completely the social and psychological aspects of cigarettes coupled with the lack of a surge or spike of nicotine high that can only be obtained by smoking simply requires too much will power for the average individual.

To put it another way, prior art methods of administering nicotine substitutes have not been successful because these methods do not recognize and address the two-prong "addiction" of smoking. First, there are social and psychological reasons for smoking that must be initially overcome. Secondly, there is the more powerful pharmacological reason (nicotine addiction) that must then be conquered. Both the social and psychological causes of smoking, as well as the pharmacological nicotine dependence must be addressed in sequence, if a truly successful method of eliminating an individual's tobacco smoking habit and associated nicotine dependence is to be provided.

SUMMARY OF THE INVENTION

Accordingly, it is a primary object of the present invention to provide an improved method of eliminating an individual's tobacco smoking habit and associated nicotine dependence overcoming the above-described limitations and disadvantages of the prior art.

Another object of the invention is to provide an improved and more effective method for overcoming the smoking habit.

Still another object of the invention is to provide a method of breaking the smoking habit that is less traumatic to the individual and that is effective for both the short and long term.

A further object of the invention is to provide a method of eliminating an individual's tobacco smoking habit through first overcoming the social and psychological reasons for smoking, and then overcoming the nicotine dependence associated with smoking.

Yet another object of the invention is to provide a method especially tailored for eliminating an individual's tobacco smoking habit where that individual is a particularly heavy smoker.

Additional objects, advantages and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, an improved method is provided for eliminating an individual's tobacco smoking habit, as well as the nicotine dependency associated with that habit. The method includes the step of gradually decreasing tobacco consumption over a first time period until no further tobacco is consumed. During this first time period, the method includes the additional step of administering an alternative nicotine source as a substitute for the tobacco consumption. Thus, the first part of the method can be referred to as the nicotine substitution phase.

Advantageously, since the body is still receiving some nicotine, albeit in more controlled doses, the social and psychological reasons for smoking can be addressed and overcome at this time. As such, the individual is more likely to succeed in eliminating the tobacco smoking habit since he is not being required to simultaneously completely overcome the nicotine dependency associated with smoking tobacco.

Further, since the tobacco consumption is only decreased gradually, there is less trauma for the individual. As such, the anxiety to which the individual is subjected, as well as the irritability that is experienced remains at a minimum.

Subsequent to the above steps in the substitution phase, the method continues with the step of gradually decreasing the administration of the alternative nicotine source over a second period of time until no further nicotine is consumed. Since the social and psychological reasons for smoking have already been addressed and overcome, it is now easier for the individual to overcome his nicotine dependency. As such, the overall method provides a far more effective means for eliminating an individual's tobacco smoking habit.

More specifically, the method includes the step of taking the alternative nicotine source orally. Preferably, the nicotine source is in the form of chewing gum as, for example, manufactured and sold under the trademark Nicorette. In accordance with the broader aspects of the invention, the nicotine alternate can be an equivalent substance, and the substance containing nicotine or not, can be administered by any process that allows introduction of the substance through mucous membranes or external exposed body tissues. This includes suppository, snuff, transdermal patch, lozenge, sucker or the like.

Prior to initating the first phase of the method, that is decreasing tobacco consumption and administering the alternative nicotine source, the individual records his or her normal tobacco consumption pattern in order to identify the times of day during which tobacco consumption occurs. Preferably, the consumption pattern is recorded for approximately two (2) weeks to ensure that the characteristics of the individual's smoking habit are accurately represented. Each day is broken down into consumption periods of one hour each. The recording of the individual's tobacco, and alternative nicotine source, consumption during each day continues throughout the performance of the method.

The tobacco consumption is gradually decreased by initially replacing the use of tobacco during the first consumption period with the alternative nicotine source. Over succeeding days, the alternative nicotine source is progressively administered as a substitute for the tobacco consumed. Specifically, progressive alternative nicotine administration occurs at a rate of one additional consumption period per day over a time period of approximately 14-16 days until no further tobacco is consumed.

Upon the complete elimination of smoking and substitution of the alternative nicotine source for tobacco consumption, the method continues with the administration of the nicotine source at the same level for approximately a four week period. During this period, the individual adjusts to the fact that he is no longer smoking and is in the process of effectively overcoming the sociological and psychological reasons that prompted smoking in the first place. Further, the individual is conditioned to receiving a steady dose of nicotine throughout the day rather than sudden nicotine spikes or peaks from smoking. Advantageously, it is easier to address and reverse nicotine addiction from this steady level by simply retraining the individual over time to accept progressively less each day.

Thus, having completely overcome the social and psychological barriers to the elimination of the smoking habit, the individual now directs complete attention to the nicotine dependency created through smoking. As discussed above, this dependency is overcome by gradually decreasing the administration of the nicotine source. The initial step in this decrease is eliminating the administration of the alternative nicotine source only during the first consumption period each day for the period of one week. The administration is then progressively eliminated during sequential consumption periods over each succeeding week until no further alternative nicotine source is consumed. The progressive elimination occurs at a rate of one additional consumption period per week for approximately fourteen to sixteen weeks. At the end of this time, the nicotine dependency of the individual is overcome and the individual's tobacco smoking habit has been successfully eliminated.

A different procedure may be utilized to eliminate the smoking habit where the individual is a relatively heavy smoker. As with the procedure previously discussed, this procedure beings with the individual recording his or her normal tobacco consumption pattern in order not only to identify the times of day during which tobacco is consumed, but also the amount of tobacco consumed. Preferably, the consumption pattern is recorded to approximately two weeks to ensure that the characteristics of the individual's smoking habit are accurately represented. Each day is broken down into consumption periods of one hour each.

The next phase in the alternative procedure includes the replacing of tobacco consumption. This is done by the combined step of abruptly stopping all tobacco consumption and administering an alternative nicotine source at a first maintenance level (i.e. from approximately 1.5 to 1.75 mg. of nicotine per consumption period) during a second period of time (a period of substantially two weeks in length). By proceeding in this manner and maintaining this dosage of substitute nicotine source, the individual is allowed to concentrate on breaking the smoking habit and overcoming his or her fears of stopping smoking without being subjected to nicotine withdrawal symptoms.

At the end of the first maintenance period, the procedure continues with the step of gradually decreasing the administration of the alternative nicotine source down to a second maintenance level of approximately 1 mg. per consumption period during a third period of time of approximately 10-18 days. More specifically, a portion of the alternative nicotine source is progressively eliminated during sequential consumption periods over each succeeding day. Preferably, substantially 0.5 to 0.75 mg. of nicotine is eliminated during each consumption period so that at the end of this phase, the individual is still receiving substantially 1 mg of nicotine during each consumption period.

After this initial gradual decrease of administration of the alternative nicotine source, the alternative nicotine source is administered at a second maintenance level of approximately 1 mg of nicotine per consumption period for a fourth period of time of substantially two weeks in length. At the end of this second maintenance phase, the method concludes with the step of progressively eliminating administration of the alternative nicotine source during a fifth period of time until no further alternative nicotine source is consumed.

More specifically, administration of the alternative nicotine source is progressively eliminated during sequential consumption periods over each succeeding week until no further alternative nicotine source is consumed. In accordance with this procedure, the progressive elimination step lasts substantially 10-18 weeks in length. Advantageously, by following this regimented procedure for the elimination of the alternative source of nicotine, the relatively heavy smoker individual is allowed to defeat his or her dependence on nicotine while suffering minimum adverse effects from withdrawal symptoms.

Still other objects of the present invention will become readily apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modifications in various, obvious aspects all without departing from the invention. Accordingly, the drawing and descriptions will be regarded as illustrative in nature and not as restrictive.

BRIEF DESCRIPTION OF THE DRAWING

The accompanying drawing incorporated in and forming a part of this specification, illustrates several aspects of the present invention, and together with the description serves to explain the principles of the invention. In the drawing:

FIG. 1 is a chart demonstrating the anti-smoking habit method of the present invention.

FIG. 2 is a chart demonstrating the antismoking habit method of the present invention particularly adapted for use with relatively heavy smokers.

Reference will now be made in detail to the present preferred embodiment of the invention, an example of which is illustrated in the accompanying drawing.

DETAILED DESCRIPTION OF THE INVENTION

Reference is now made to FIG. 1 so as to further illustrate the structured pattern method of the present invention for eliminating an individual's tobacco smoking habit, as well as the nicotine dependence associated therewith. The method is being described with respect to an individual presently smoking approximately 30 cigarettes per day. Of course, it should be appreciated that the method is equally applicable to other individuals with different smoking habits simply by varying the method as will be clear from the following.

In brief, the method begins with a two week qualification phase wherein the individual records the time during which each cigarette is consumed during the day thereby reflecting the individual's tobacco consumption pattern. During this two week phase the individual continues to smoke normally.

During the following two week phase, an alternative nicotine source, such as a nicotine gum substitute (NGS), is gradually administered to the individual while cigarettes are gradually phased out. Specifically, as the alternative nicotine source (NGS) is phased in, tobacco consumption is gradually decreased until no further tobacco is consumed.

Following complete substitution, there is a four week maintenance phase wherein the individual is allowed to adjust and overcome the social and psychological causes of smoking. During this phase no cigarettes are consumed, but the individual continues to receive the full dose of nicotine through NGS. As such, the individual is not under the pharmacological pressure to smoke in order to obtain the established daily requirement of nicotine. Only after overcoming the social and psychological pressures to smoke is this nicotine dependency addressed.

During the remaining fifteen weeks of the method, the nicotine dependency can then be addressed and successfully overcome. This relatively slow, stepped approach is very advantageous in overcoming nicotine dependency. When smoking first begins, the individual does not immediately begin by smoking 30 cigarettes a day. Such large consumption of nicotine without prior use would likely make the person nauseous. Instead, a smoker develops a habit of smoking up to 30 cigarettes a day by gradually increasing the number of cigarettes consumed over time as nicotine dependency develops. The present method recognizes this aspect of nicotine dependency and provides a structured, systematic approach for steadily decreasing nicotine consumption until nicotine dependency is overcome.

In order to provide still more detail of the method, reference is now made back to the start, that is to the period of qualification wherein the individual continues to smoke normally. During this period, the individual's tobacco consumption pattern is determined by recording the time of day during which each cigarette is smoked. Preferably a chart (not shown) is used broken down into consumption periods of one hour each. Thus, for example, if the first cigarette is smoked during the drive to work at 7:30 A.M., one cigarette is noted in the consumption period between 7:00 A.M. and 8:00 A.M.

After faithfully recording tobacco consumption pattern each day for two consecutive weeks, the individual has sufficient information upon which specifically to identify all of the consumption periods for each day of the week. With this information, the individual can successfully implement the remaining portion of the anti-smoking method of the present invention.

For a smoker who consumes approximately 30 cigarettes a day in sixteen consumption periods, the present method of stopping smoking lasts approximately 24 weeks. During the two weeks following qualification, the individual proceeds through the substitution phase. On the first day of the substitution phase, one NGS (Nicorette) including 2 mg of nicotine is administered to the individual and slowly chewed throughout the first consumption period. Essentially the nicotine in the Nicorette is substituted for all tobacco consumed during the first consumption period. For the remainder of the first day, tobacco consumption continues normally without the administration of any other nicotine source.

During the succeeding days of the substitution phase, NGS is administered in increasing doses as a substitute for tobacco consumed up to the full 16 consumption periods, i.e. until no further tobacco is consumed (note declining cigarette line and rising NGS line in FIG. 1). Thus, on the second day of the substitution phase, NGS is administered during the first two consumption periods as a substitute for cigarettes and cigarette smoking continues normally for the remainder of the day. On the third day Nicorettes are substituted for cigarettes during the first three consumption periods; and so forth, for the following days until no further cigarettes are actually being consumed. Assuming it was determined during the qualification period that the individual smokes his first cigarette of the day during the consumption period between 7:00 A.M. and 8:00 A.M. and his last cigarette of the day during the consumption period between 10:00 P.M. and 11:00 P.M., it would take two weeks and two days to completely substitute the NGS for cigarettes.

Following complete substitution, the method contemplates a maintenance phase of approximately four weeks. During this four week period, the NGS (for example, in the form of Nicorettes) continues to be administered to the individual as a substitute for all cigarettes consumed. Thus, throughout this four week period, the individual is no longer smoking any cigarettes, yet the nicotine is still being received. As such, the individual must only deal with completing the adjustment to the social and psychological causes of his smoking at this time. Only after this is conquered is the problem of nicotine dependency addressed.

Following the four week maintenance phase during which the individual adjusts to receiving a steady level of nicotine, the method continues with the gradual decrease in the administration of NGS until no further NGS and, therefore, nicotine is consumed. As shown in FIG. 1, this phase lasts approximately 15 weeks. During the first week, no NGS is administered during the first consumption period, previously identified during the qualification phase. NGS does, however, continue to be administered during the remaining consumption periods of the day.

Over the remaining 14 weeks of this phase, the administration of the NGS is progressively eliminated. Specifically, the elimination takes place during sequential consumption periods over each succeeding week. Thus, during the second week, no NGS are administered during each of the first two consumption periods of the day but NGS administration continues over the remaining consumption periods of the day. During the third week no NGS are administered through the first three consumption periods of the day, during the fourth week during the first four periods and so on until no further alternative nicotine source is consumed. At this point in time, both the individual's smoking habit, as well as the associated nicotine dependency, are overcome and the treatment has been successfully completed.

Preferably throughout the entire method, the individual continues to record consumption of cigarettes and NGS for each consumption period so as to chart the progress. After completing the method, the individual then has a record of the accomplishment in which pride can be taken. Further, throughout the phases of this method, the record serves as positive reinforcement for following the method to its completion.

An alternative method of eliminating an individual's tobacco smoking habit and associated nicotine dependence may be utilized where the individual is a relatively heave smoker (see FIG. 2). Many relatively heavy smokers (i.e. more than 30 cigarettes per day), smoke a large number of cigarettes early in the morning. Many have also tried to quit smoking a number of times previously and are not only afraid of another failure, but equally fearful of giving up smoking. In addition, many relatively heavy smokers may experience the classical symptoms of physical withdrawal from the addicting nicotine contained in cigarettes even when following the above-described improved smoking cessation method. These symptoms include intense craving, restlessness and irritability.

Of course, even though this alternative procedure works extremely well for relatively heavy smokers, it is not limited to this class. Indeed, it has in fact been successfully utilized by other smokers experiencing nicotine withdrawal symptoms and exceeds the results expected when following other methods.

During the initial phases of this alternative procedure, the individual continues to smoke normally during a two week period of time. During this period, the individual's tobacco consumption pattern is determined by recording the time of day during which each cigarette is smoked. As set forth above with respect to the previously discussed method, a chart is utilized to break down each day into consumption periods of one hour each. Thus, for example, if the first cigarette is smoked in the morning at 6:30 A.M., one cigarette is noted in the consumption period between 6:00 A.M. and 7:00 A.M. Of course, additional cigarettes also smoked during this period would be recorded.

After faithfully recording his or her tobacco consumption pattern each day for two consecutive weeks, the individual has sufficient information upon which specifically to identify the number of cigarettes smoked during all of the consumption periods for each day of the week. With this information, the individual can successfully implement the remaining portion of the alternative anti-smoking method of the present invention.

For purposes of example, we assume that during the recording phase, the individual determines that he or she smokes approximately 50 cigarettes a day in sixteen (16) consumption periods (i.e. 16 waking hours). Of course, this assumption is only being utilized to describe the alternative procedure of the present invention and is not to be considered limiting in any way.

After the recording phase, the individual begins replacing tobacco consumption by administering an alternative nicotine source at a first maintenance level for a period of time of substantially two weeks in length. In practicing this embodiment of the invention, it is a new feature to provide the relatively heavy smokers with a higher initial level of nicotine from the alternative nicotine source. Secondly, the smoker abruptly stops smoking on the first day of this two week period and immediately begins the administration of the alternative nicotine source as the sole source. More specifically, every waking hour or consumption period, the individual utilizes one 2 mg. piece of Nicorette gum. On the half hour he or she replaces that whole piece of Nicorette gum with one ¾ piece of Nicorette gum. For a 16 consumption period day, this represents 16 whole pieces plus 16 ¾ pieces for a total of 28 pieces of the alternative nicotine source. This is below the 30 piece maximum set by the FDA.

While the Nicorette gum officially contains a total of 2 mg. of nicotine, only approximately 1-1.05 mg. nicotine can be abstracted from each whole piece of Nicorette gum. The reason for this is that the amount of nicotine available for absorption from the gum into the bloodstream via the buccal mucosa is limited by the supply of the buffering agent, sodium bicarbonate. Based on on this, it should be appreciated that the individual receives approximately 28-29.4 mg. of nicotine per day from the Nicorette gum when utilized as described above. This higher level of nicotine administration from an alternative source when compared to the previously described method dramatically reduces the classical symptoms of physical withdrawal from the nicotine in heavy smokers. Advantageously, this allows the heavy smokers to concentrate on overcoming the smoking habit during this second two-week period oft he program. It also provides the heavy smoker with the confidence necessary to break the smoking habit.

At the end of the first maintenance period wherein the individual administers 1 ¾ pieces of Nicorette gum per consumption period, the procedure continues with the step of gradually decreasing the administration of the alternative nicotine source down to a second maintenance level of approximately 1-1.05 mg. of nicotine per consumption period. This step of the method is completed over a period of time of approximately 10-18 days, depending on the number of consumption periods.

More specifically, on the first day of this phase of the method, only one piece of Nicorette gum is chewed during the first consumption period with the ¾ piece of Nicorette gum eliminated. On the second day, the ¾ piece of Nicorette gum is eliminated from use during the first two consumption periods. This progressive elimination continues day-to-day until only one piece of Nicorette gum is utilized for each consumption period throughout the 16 consumption periods. Thus, at the end of this phase of the procedure, the individual is still receiving one piece of Nicorette gum or substantially 1-1.05 mg. of nicotine during each consumption period or a total of 16-16.8 mg. of nicotine per day.

After this initial gradual decrease of administration of the alternative nicotine source, the alternative nicotine source is administered at a second maintenance level of approximately 1-1.05 mg. of nicotine per consumption period for a period of time of substantially two weeks in length. Advantageously, this plateau of administration of nicotine through the alternative nicotine source allows the addiction of the individual to stabilize at a lower nicotine level before attempting to actually eliminate the individual's nicotine dependence. This serves to greatly reduce the intense craving, restlessness and irritability of the individual. As a result, the individual's confidence in breaking the smoking habit and the associated nicotine dependence grows.

At the end of the second maintenance phase, the method concludes with the step of progressively eliminating administration of the alternative nicotine source during a final or fifth period of time until no further alternative nicotine source is consumed, as shown in FIG. 2. In accordance with this procedure, the progressive elimination step lasts substantially 10-18 weeks in length, depending on the number of consumption periods for the individual.

The elimination phase utilized is exactly as described above in the previously discussed method. More specifically, during the first week, no Nicorette gum is administered during the first consumption period of each day previously identified during the recording phase. Administration of Nicorette gum does, however, continue during the remaining consumption periods of each day. Over the remaining weeks of this phase, the administration of Nicorette gum is progressively eliminated (see FIG. 2).

To further explain, using the same regimen as the example, during the second week no Nicorette gum is administered during each of the first two consumption periods of the day, but Nicorette gum is administered over the remaining consumption periods of the day. During the third week, no Nicorette gum is administered through the first three consumption periods of the day, during the fourth week during the first four periods and so on until no further alternative nicotine source is consumed. At this point in time, both the individual's smoking habit as well as the associated nicotine dependency, are overcome and the treatment has been successfully completed.

Of course, as discussed above, throughout the entire method, the individual continues to record consumption of cigarettes or Nicorette gum for each consumption period so as to document the regimen and to chart his or her progress. Throughout the phases of this alternative method, the record serves as positive reinforcement for following the method to its completion.

In summary, numerous benefits have been described which result from employing the concepts of the invention. The method reduces the stress to which an individual is subjected during the process of stopping smoking. Specifically, the method allows the individual to first overcome the social and psychological causes for smoking and then, and only then, is there a need to address and overcome the nicotine dependency associated with smoking. By approaching these causes one at a time, individuals can successfully stop smoking.

The foregoing description of a preferred embodiment of the invention has been presented for purposes of illustration and description. It is not intended to be exhaustive or to limit the invention to the precise form disclosed. Obvious modifications or variations are possible in light of the above teachings. For example, various phases of the method may be adjusted in length in order to reflect differences in the smoking pattern of the individual. Further, alternative nicotine sources may include equivalent substances including any and all known compounds and/or compositions, such as lobeline sulfate. These substances produce a similar physiological effect and may be substituted for the NGS in accordance with the broader aspects of the invention. The embodiment was chosen and described to provide the best illustration of the principles of this invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

We claim:

1. A method of eliminating an individual's tobacco smoking habit and associated nicotine dependence in a structured pattern, comprising the steps of:
   breaking a day down into consumption periods;
   recording an individual's tobacco consumption for each consumption period during a first period of time;
   replacing tobacco consumption by administering an alternative nicotine source at a first maintenance level during a second period of time;
   gradually decreasing administration of said alternative nicotine source down to a second maintenance level during a third period of time;
   administering said alternative nicotine source at said second maintenance level for a fourth period of time; and
   progressively eliminating administration of said alternative nicotine source during a fifth period of time until no further alternative nicotine source is consumed.

2. The method set forth in claim 1, wherein each consumption period is one hour long.

3. The method set forth in claim 1, wherein said first period of time is substantially two weeks in length.

4. The method set forth in claim 2, wherein tobacco consumption is abruptly stopped and said first maintenance level of alternative nicotine source is substantially equivalent to receiving 1.5 to 1.75 mg. of nicotine per consumption period.

5. The method set forth in claim 4, wherein said second period of time is substantially two weeks in length.

6. The method set forth in claim 2, wherein said step of gradually decreasing administration of said alternative nicotine source includes a step of progressively eliminating a portion of said alternative nicotine source during sequential consumption periods over each succeeding day.

7. The method set forth in claim 6, wherein substantially 0.5 to 0.75 mg. of nicotine is eliminated during sequential consumption periods over each succeeding day.

8. The method set forth in claim 6, wherein said third period of time is substantially 10 to 18 days in length.

9. The method set forth in claim 2, wherein said second maintenance level of alternative nicotine source is substantially equivalent to receiving 1.0 mg of nicotine per consumption period.

10. The method set forth in claim 9, wherein said fourth period of time is substantially two weeks in length.

11. The method set forth in claim 2, wherein said step of progressively eliminating administration of said alternative nicotine source includes a step of progressively eliminating administration of said alternative nicotine source during sequential consumption periods over each succeeding week until no further alternative nicotine source is consumed.

12. The method set forth in claim 11, wherein said fifth period of time is substantially 10 to 18 weeks in length.

* * * * *